US012385840B2

(12) United States Patent
Suenaga et al.

(10) Patent No.: US 12,385,840 B2
(45) Date of Patent: Aug. 12, 2025

(54) RESIN COMPOSITION QUALITY CONTROLLING METHOD, CABLE AND TUBE QUALITY CONTROLLING METHOD, DETERMINATION DEVICE, INSPECTION SYSTEM, AND CABLE AND TUBE

(71) Applicant: Hitachi Metals, Ltd., Tokyo (JP)

(72) Inventors: Kazufumi Suenaga, Tokyo (JP); Seiichi Kashimura, Tokyo (JP)

(73) Assignee: Proterial, Ltd., Tokyo (JP)

( * ) Notice: Subject to any disclaimer, the term of this patent is extended or adjusted under 35 U.S.C. 154(b) by 446 days.

(21) Appl. No.: 17/945,574

(22) Filed: Sep. 15, 2022

(65) Prior Publication Data

US 2023/0093012 A1 Mar. 23, 2023

(30) Foreign Application Priority Data

Sep. 17, 2021 (JP) ................................. 2021-151927

(51) Int. Cl.
*G01N 21/65* (2006.01)
*G01N 33/00* (2006.01)

(52) U.S. Cl.
CPC .......... *G01N 21/65* (2013.01); *G01N 33/0003* (2024.05); *G01N 33/0078* (2024.05); *G01N 33/0096* (2024.05)

(58) Field of Classification Search
CPC .. G01N 21/65; G01N 2021/8405; C08K 3/22; C08K 2003/2241; C08K 2201/014
See application file for complete search history.

(56) References Cited

U.S. PATENT DOCUMENTS

| | | | | | |
|---|---|---|---|---|---|
| 5,579,429 | A | * | 11/1996 | Naum | G02B 6/3855 385/127 |
| 5,981,426 | A | * | 11/1999 | Langford | B01J 35/39 502/4 |
| 6,281,277 | B1 | * | 8/2001 | Ishii | C08K 9/02 423/625 |
| 11,041,091 | B2 | | 6/2021 | Kashimura et al. | |
| 2004/0226813 | A1 | * | 11/2004 | Wang | B01J 35/58 428/690 |
| 2010/0102251 | A1 | * | 4/2010 | Ferrini | H05B 33/22 427/164 |

(Continued)

FOREIGN PATENT DOCUMENTS

JP 6723489 B1 6/2020

OTHER PUBLICATIONS

5. Yu, Bin, et al. "Influence of TiO2 nanoparticles on the optical properties of resin composites." Dental Materials 25.9 (2009): 1142-1147 (Year: 2009).*

*Primary Examiner* — Kara E. Geisel
*Assistant Examiner* — Roberto Fabian, Jr.
(74) *Attorney, Agent, or Firm* — Studebaker Brackett PLLC

(57) ABSTRACT

A resin composition quality controlling method includes a step of measuring a Raman spectrum of a resin composition composed of $TiO_2$ particles dispersed in a base material mainly composed of a silicone rubber by irradiating the resin composition with laser, and a step of determining a concentration of the $TiO_2$ particles in the resin composition based on an intensity of a fluorescence spectrum in the Raman spectrum.

13 Claims, 15 Drawing Sheets

(56) References Cited

U.S. PATENT DOCUMENTS

| | | | |
|---|---|---|---|
| 2016/0166482 A1* | 6/2016 | Shenderova | C09D 7/67 |
| | | | 435/7.1 |
| 2017/0007724 A1* | 1/2017 | Achilefu | A61K 41/0057 |
| 2021/0079258 A1 | 3/2021 | Kashimura et al. | |
| 2021/0079260 A1 | 3/2021 | Kashimura et al. | |
| 2021/0207000 A1 | 7/2021 | Kashimura et al. | |
| 2021/0238446 A1 | 8/2021 | Kashimura et al. | |
| 2022/0145127 A1 | 5/2022 | Kashimura et al. | |

* cited by examiner

RESIN COMPOSITION QUALITY CONTROLLING METHOD, CABLE AND TUBE QUALITY CONTROLLING METHOD, DETERMINATION DEVICE, INSPECTION SYSTEM, AND CABLE AND TUBE

CROSS-REFERENCE TO RELATED APPLICATIONS

The present patent application claims the priority of Japanese patent application No. 2021-151927 filed on Sep. 17, 2021, and the entire contents thereof are hereby incorporated by reference.

TECHNICAL FIELD

The present invention relates to a resin composition quality controlling method, a cable and tube quality controlling method, a determination device, an inspection system, and a cable or a tube.

BACKGROUND ART

A cable for a medical device, which includes a sheath comprising a material blended with an infrared absorbing agent such as titanium dioxide ($TiO_2$), has been conventionally known (see Patent Literature 1). According to Patent Literature 1, adding the infrared absorbing agent to the sheath allows a coating film on the sheath to be heated also from the sheath side and curing of a portion of the coating film on the sheath side to be accelerated at the time of heating the coating film with infrared rays. The adhesion strength between the coating film and the sheath is thereby improved.

CITATION LIST

Patent Literature

Patent Literature 1: Japanese Patent No. 6723489

SUMMARY OF INVENTION

In recent years, sterilization by irradiation with ultraviolet light in the UV-C region (UV-C light), which allows for simple, inexpensive, and reliable sterilization, has attracted attention as a method for sterilizing cables and tubes for medical devices, but to perform sterilization by irradiation with UV-C light, the resistance of cables and tubes to UV-C light becomes a problem. It is known that when deterioration due to irradiation with UV-C light progresses, cracks occur in an insulator at the time of, e.g., bending cables or tubes. For this reason, a resin composition with excellent resistance to UV-C light are desired to be used as insulators of cables or tubes.

Therefore, it is an object of the invention to provide a resin composition quality controlling method for a resin composition including $TiO_2$ added as an ultraviolet light shielding material to provide a resin composition having excellent resistance to UV-C light and in which a decrease in percent elongation and quality is suppressed, a determination device and an inspection system which can be used for the method for controlling quality of such a resin composition, a cable and tube quality controlling method for a cable or a tube each including, as an insulator, a resin composition including $TiO_2$ added as an ultraviolet light shielding material to provide a cable and a tube each having excellent resistance to UV-C light and in which a decrease in percent elongation and quality of the insulator is suppressed, and a cable and a tube each of which includes, as an insulator, a resin composition including $TiO_2$ added as an ultraviolet light shielding material and has excellent resistance to UV-C light and in which a decrease in percent elongation and quality of the insulator is suppressed.

So as to achieve the above object, one aspect of the invention provides: a resin composition quality controlling method, comprising:
  measuring a Raman spectrum of a resin composition comprising $TiO_2$ particles dispersed in a base material comprising mainly a silicone rubber by irradiating the resin composition with laser; and
  determining a concentration of the $TiO_2$ particles in the resin composition based on an intensity of a fluorescence spectrum in the Raman spectrum.

So as to achieve the above object, another aspect of the invention provides: a cable and tube quality controlling method, comprising:
  determining a concentration of the $TiO_2$ particles in an insulator being provided on a cable or a tube and comprising the resin composition by the resin composition quality controlling method.

So as to achieve the above object, still another aspect of the invention provides: a determination device configured to perform the determining in the resin composition quality controlling method.

So as to achieve the above object, a further aspect of the invention provides: an inspection system, comprising:
  a Raman measurement device configured to perform the measuring in the resin composition quality controlling method according to claim 1; and
  a determination device configured to perform the determining in the resin composition quality controlling method according to claim 1.

So as to achieve the above object, a still further aspect of the invention provides: a cable and a tube each comprising:
  an insulator comprising a resin composition comprising $TiO_2$ particles dispersed in a base material comprising mainly a silicone rubber,
  wherein a concentration of the $TiO_2$ particles in the insulator is within a range of 3.4 to 8.1 mass %.

Effects of the Invention

According to the present invention, it is possible to provide a resin composition quality controlling method for a resin composition including $TiO_2$ added as an ultraviolet light shielding material to provide a resin composition having excellent resistance to UV-C light and in which a decrease in percent elongation and quality is suppressed, a determination device and an inspection system which can be used for the method for controlling quality of such a resin composition, a cable and tube quality controlling method for a cable or a tube each including, as an insulator, a resin composition including $TiO_2$ added as an ultraviolet light shielding material to provide a cable and a tube each having excellent resistance to UV-C light and in which a decrease in percent elongation and quality of the insulator is suppressed, and a cable and a tube each of which includes, as an insulator, a resin composition including $TiO_2$ added as an ultraviolet light shielding material and has excellent resistance to UV-C light and in which a decrease in percent elongation and quality of the insulator is suppressed.

DESCRIPTION OF EMBODIMENTS

First Embodiment

Configuration of Resin Composition

Figure 1A:
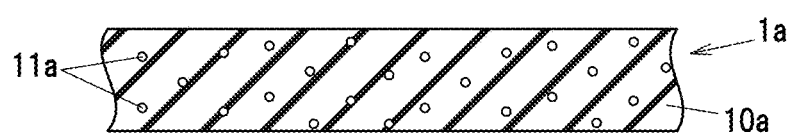
FIG. 1A is a vertical cross-sectional view showing a resin composition according to the first embodiment of the present invention.

FIG. 1A is a vertical cross-sectional view showing a resin composition 1a in the first embodiment of the invention. The resin composition 1a includes a base material 10a made of silicone rubber, and $TiO_2$ particles 11a included in the base material 10a.

Figure 1B:
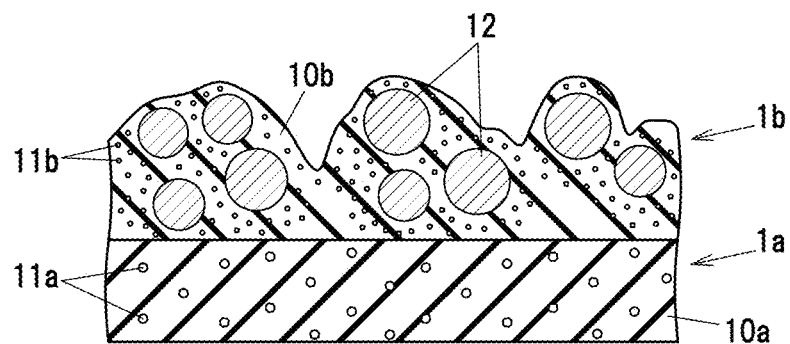
FIG. 1B is a vertical cross-sectional view showing two stacked resin compositions in the first embodiment of the invention.

FIG. 1B is a vertical cross-sectional view showing the resin composition 1a and resin composition 1b in the first embodiment of the invention, which are stacked. The resin composition 1b includes a base material 10b made of silicone rubber, $TiO_2$ particles 11b included in the base material 10b, and irregularity-forming particles 12 such as silicone resin particles to form irregularity (i.e., unevenness) on a surface to improve sliding properties.

The $TiO_2$ particles 11a, 11b as an ultraviolet light shielding material to shield UV-C light by absorption and/or scattering are added to the resin compositions 1a, 1b, respectively. $TiO_2$ has a higher scattering coefficient for ultraviolet light than white pigment ZnO or silicone resin and has an excellent ultraviolet light shielding function. A particle diameter of the $TiO_2$ particles 11a, 11b is, e.g., 10 to 500 nm.

The $TiO_2$ particles 11a, 11b may be either anatase type $TiO_2$ particles or rutile type $TiO_2$ particles, or may include both. Anatase type $TiO_2$ has a higher absorbance of ultraviolet light in the UV-C region (200 to 280 nm) than rutile type $TiO_2$ Meanwhile, rutile type $TiO_2$ can absorb longer wavelength ultraviolet light, as compared to anatase type $TiO_2$ (rutile type $TiO_2$ can absorb ultraviolet light at about not more than 400 nm, while anatase type $TiO_2$ can absorb ultraviolet light at about not more than 370 nm). When the $TiO_2$ particles 11a, 11b include both anatase type $TiO_2$ particles and rutile type $TiO_2$ particles, the resin compositions 1a, 1b have excellent resistance to UV-C light and also have resistance to ultraviolet light in a wide wavelength range.

The base materials 10a, 10b are made of silicone rubber, as described above. When the resin compositions 1a, 1b are used as cable insulator (e.g., a sheath and a coating film thereon), common compounding agents such as various cross-linking agents, cross-linking catalysts, antioxidants, plasticizers, lubricants, fillers, flame retardants, stabilizers, and colorants may be added to the base materials 10a, 10b.

The resin composition 1a, which includes the TiO$_2$ particles 11a and has excellent resistance to UV-C light, is suitably used as, e.g., an insulator of a cable or a tube. The resin composition 1a and the resin composition 1b stacked thereon are shown in FIG. 1B are, e.g., respectively used as a sheath and a coating film thereon, which are insulators of a cable.

The resin compositions 1a, 1b can be in various forms depending on their intended use.

The resin compositions 1a, 1b are molded into, e.g., a tube shape when used as an insulator of a cable or a tube, and are molded into a sheet shape when used as a highly UV-resistant sheet for constant temperature house or an ultraviolet shielding sheet (ultraviolet shielding curtain) to shield against ultraviolet light leakage from a sterilization chamber, etc.

Method for Controlling the Quality of Resin Composition

In the resin composition quality controlling method in the first embodiment, a concentration of the TiO$_2$ particles 11a in the resin composition 1a or a concentration of the TiO$_2$ particles 11b in the resin composition 1b can be measured by Raman scattering measurement in a non-destructive, non-contact manner while maintaining the original shape of the resin compositions 1a, 1b.

The resin composition quality controlling method in the first embodiment includes, e.g., a measurement step of measuring a Raman spectrum of the resin composition (the resin composition 1a or the resin composition 1b) including TiO$_2$ particles dispersed in a base material consisting mainly of silicone rubber by irradiating the resin composition with laser, and a determination step of determining a concentration of the TiO$_2$ particles in the resin composition based on the intensity of a fluorescence spectrum in the measured Raman spectrum. Here, the intensity of the peak in Raman spectrum in the embodiments means peak height or integral intensity.

The intensity of the fluorescence spectrum in the Raman spectrum varies with the concentration of TiO$_2$ included in the resin composition. Therefore, based on this intensity of the fluorescence spectrum, it is possible to determine the concentration of the TiO$_2$ particles in the resin composition 1a or 1b.

Figure 2A:
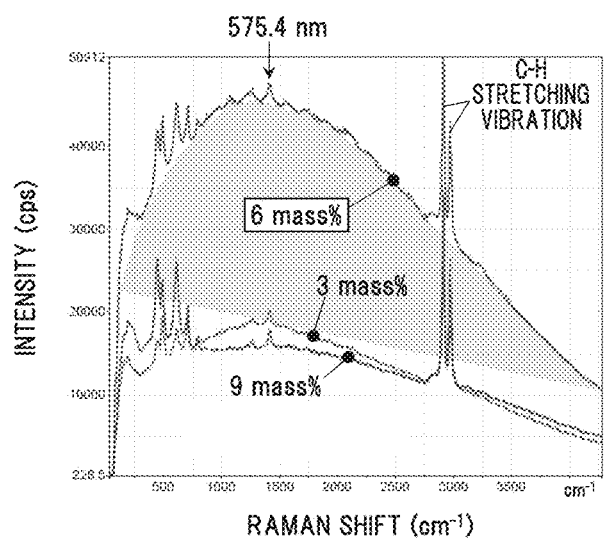
FIG. 2A shows Raman spectra of a resin composition including rutile type $TiO_2$ particles.
Figure 2B:
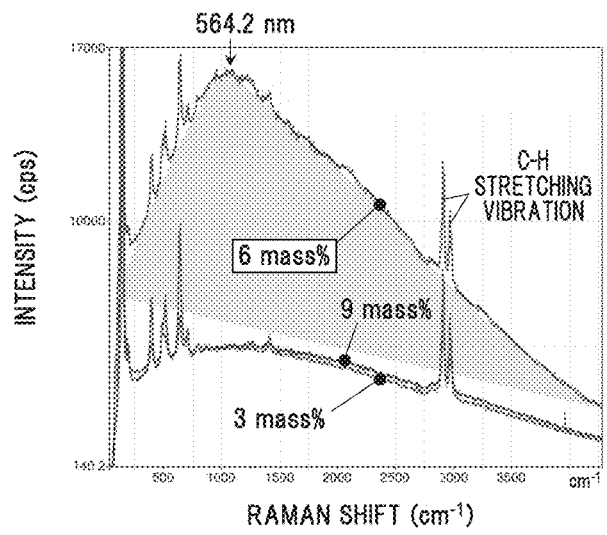
FIG. 2B shows Raman spectra of a resin composition including anatase type $TiO_2$ particles.
Figure 2C:
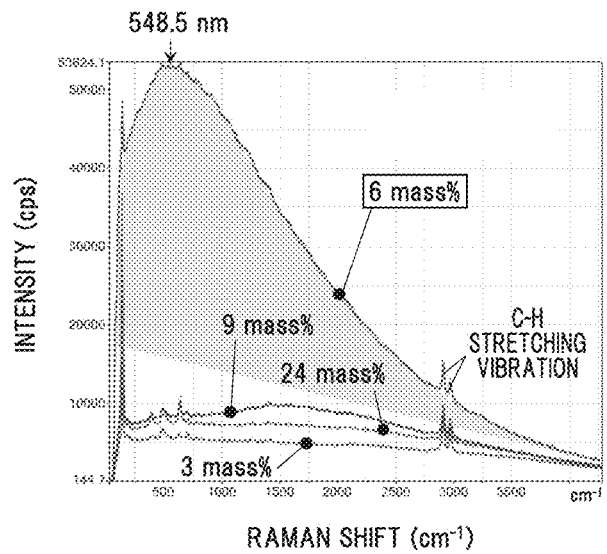
FIG. 2C shows Raman spectra of a resin composition stacked on a resin composition 1a including anatase type $TiO_2$ particles and irregularity-forming particles.

FIG. 2A shows Raman spectra of the resin composition 1a including 3 mass %, 6 mass % or 9 mass % of rutile type TiO$_2$ particles as the TiO$_2$ particles 11a. FIG. 2B shows Raman spectra of the resin composition 1a including 3 mass %, 6 mass % or 9 mass % of anatase type particles as the TiO$_2$ particles 11a. FIG. 2C shows Raman spectra of the resin composition 1b stacked on the resin composition 1a and including 3 mass %, 6 mass %, 9 mass % or 24 mass % of anatase type TiO$_2$ particles as the TiO$_2$ particles 11b. The resin composition 1b for FIG. 2C includes silicone resin particles as the irregularity-forming particles 12.

The Raman scattering measurement to obtain the spectra shown in FIGS. 2A to 2C was performed using RAMAN-force Standard VIS-NIR-HS available from Nanophoton Corporation under the following measurement conditions: a wavelength of the laser was 532 nm, a width of an incident slit of a spectrometer was 50 μm, the number of rulings in a diffraction grating was 300 gr/mm, a value of a ratio of the amount of light after attenuation to the maximum amount of laser light of an ND filter (an attenuation ratio) was 165/255 to 200/255, magnification, numerical aperture (NA) and theoretical measurement diameter of an objective lens were respectively 5×, 0.15 and 2.2 μm, a laser scanning range was about 1653 μm×1512 μm, and counting time was 1 second× 10 to 15 cycles. In addition, the Raman scattering measurement was performed in an environment where the temperature was 20° C. (an average value from 2-point measurement in an analysis laboratory), the humidity was 28 RH % (an average value from 3-point measurement in the analysis laboratory), and air pressure was normal pressure (so-called atmospheric pressure).

In the Raman spectra in each of FIGS. 2A to 2C, a high-intensity fluorescence spectrum is observed when the concentration of the TiO$_2$ particles is 6 mass %. This phenomenon, in which a high-intensity fluorescence spectrum is observed in the Raman spectrum when the concentration of the TiO$_2$ particles is around 6 mass %, is considered to be characteristic of resin compositions including TiO$_2$ particles dispersed in silicone rubber, such as the resin compositions 1a and 1b. It is a phenomenon first discovered by the present inventors.

Figure 3A:
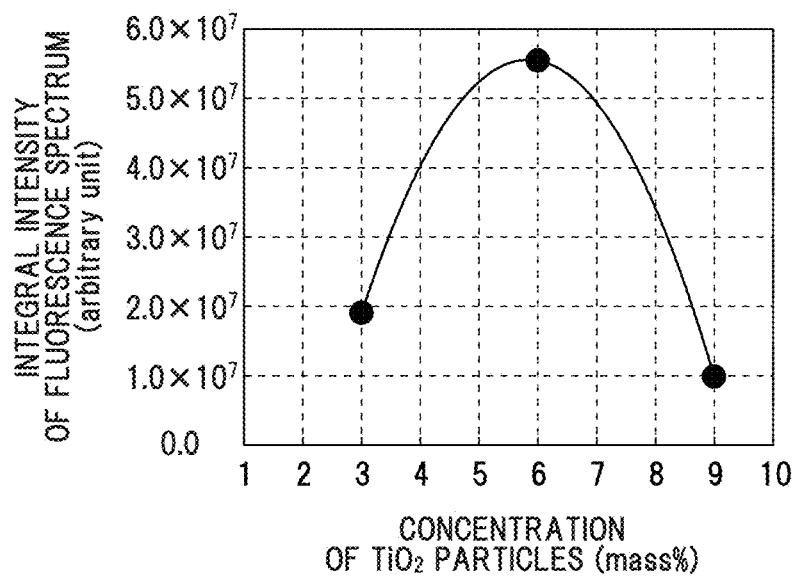
FIG. 3A is a graph showing a relationship between the integral intensity of the fluorescence spectrum in the Raman spectra of the resin composition shown in FIG. 2A and a concentration of $TiO_2$ particles in the resin composition.
Figure 3B:
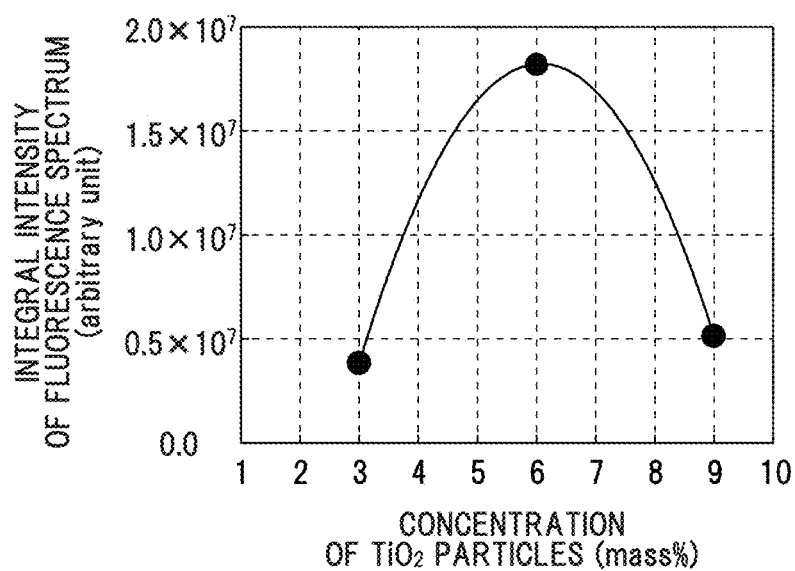
FIG. 3B is a graph showing a relationship between the integral intensity of the fluorescence spectrum in the Raman spectra of the resin composition shown in FIG. 2B and the concentration of $TiO_2$ particles in the resin composition.
Figure 4A:
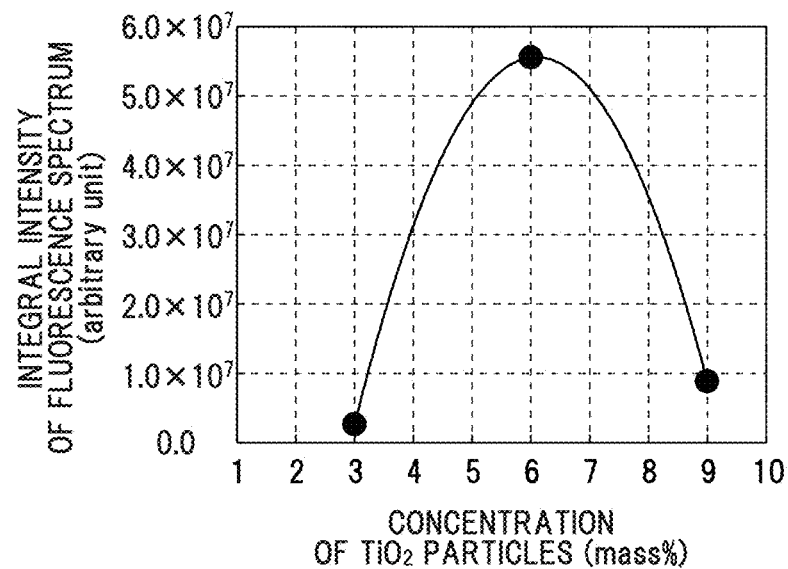
FIGS. 4A and 4B are graphs showing a relationship between the integral intensity of the fluorescence spectrum in the Raman spectra of the resin composition shown in FIG. 2C and the concentration of $TiO_2$ particles in the resin composition.
Figure 4B:
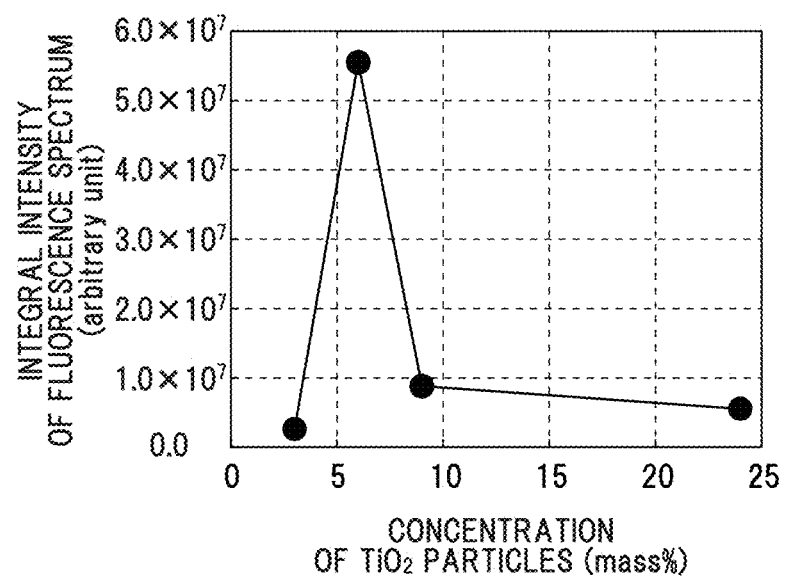

FIG. 3A is a graph showing a relationship between the integral intensity of fluorescence spectrum in the Raman spectra of the resin composition 1a including rutile type TiO$_2$ particles as the TiO$_2$ particles 11a shown in FIG. 2A and the concentration of the TiO$_2$ particles 11a in the resin composition 1a. FIG. 3B is a graph showing a relationship between the integral intensity of fluorescence spectrum in the Raman spectra of the resin composition 1a including anatase type TiO$_2$ particles as the TiO$_2$ particles 11a shown in FIG. 2B and the concentration of the TiO$_2$ particles 11a in the resin composition 1a. FIGS. 4A and 4B are graphs showing a relationship between the integral intensity of fluorescence spectrum in the Raman spectra of the resin composition 1b including anatase type TiO$_2$ particles as the TiO$_2$ particles 11b shown in FIG. 2C and the concentration of the TiO$_2$ particles 11b in the resin composition 1b.

The integral intensity of each fluorescence spectrum was obtained by fitting analysis using the Lorentz distribution function, which is performed by integrating the fluorescence spectrum over a range of 250 to 4250 cm$^{-1}$, which includes substantially the entire fluorescence spectrum. In this regard, the fitting analysis can be performed using Gauss distribution function, Lorentz distribution function, Pseudo-Voigt distribution function, or an equation expressed as a superposition of two or more of these functions according to the shape of the spectral pattern.

An approximate curve in FIG. 3A is a curve obtained by polynomial approximation using the least-square method and is expressed by the equation $y=-4.56\times10^6 x^2+5.31\times 10^7 x-9.94\times 10^7$, where x is a value on the horizontal axis and y is a value on the vertical axis. An approximate curve in FIG. 3B is a curve obtained by polynomial approximation using the least-square method and is expressed by the equation $y=-1.53\times10^6 x^2+1.85\times 10^7 x-3.80\times 10^7$, where x is a value on the horizontal axis and y is a value on the vertical axis. An approximate curve in FIG. 4A is a curve obtained by polynomial approximation using the least-square method and is expressed by the equation $y=-5.54\times10^6 x^2+6.75\times 10^7 x-1.50\times 10^8$, where x is a value on the horizontal axis and y is a value on the vertical axis.

Figure 5A:
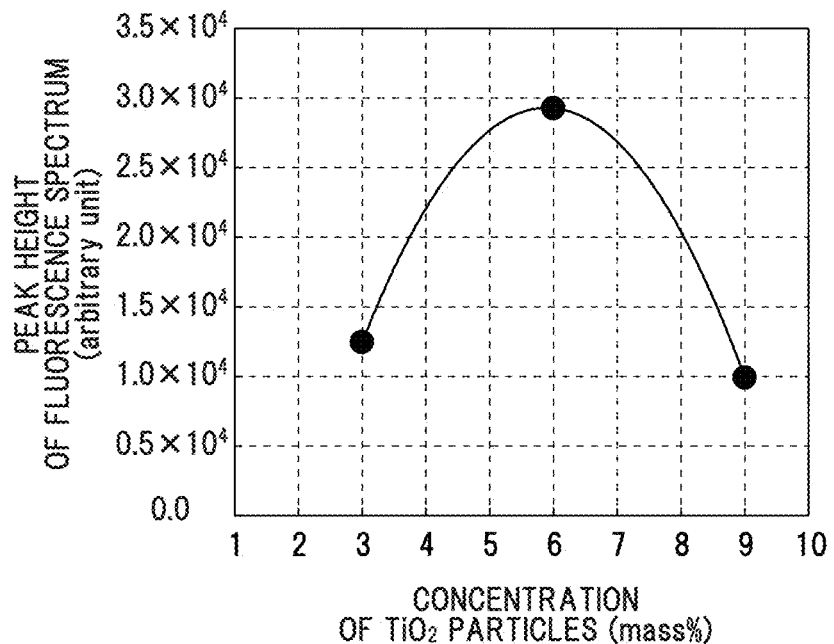
FIG. 5A is a graph showing a relationship between the peak height of the fluorescence spectrum in the Raman spectra of the resin composition shown in FIG. 2A and the concentration of $TiO_2$ particles in the resin composition.
Figure 5B:
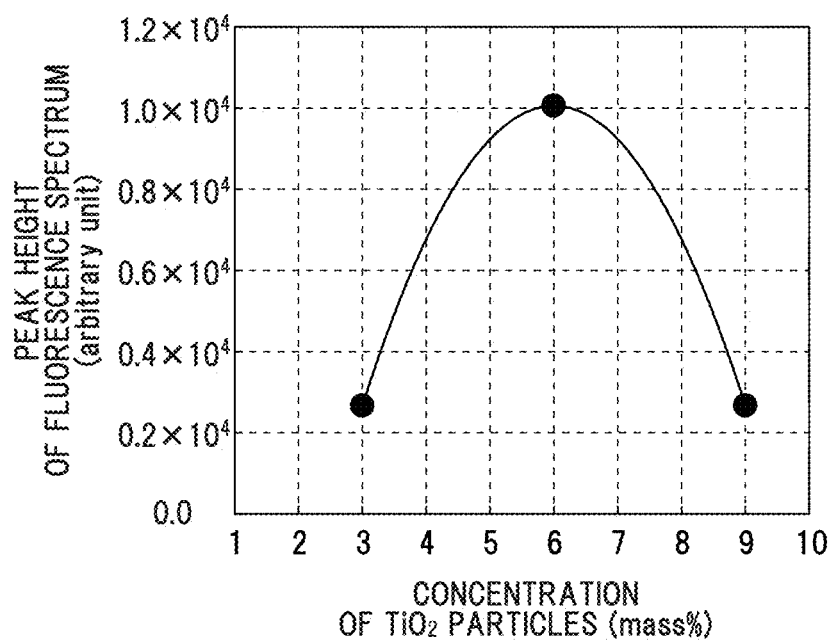
FIG. 5B is a graph showing a relationship between the peak height of the fluorescence spectrum in the Raman spectra of the resin composition shown in FIG. 2B and the concentration of $TiO_2$ particles in the resin composition.
Figure 6A:
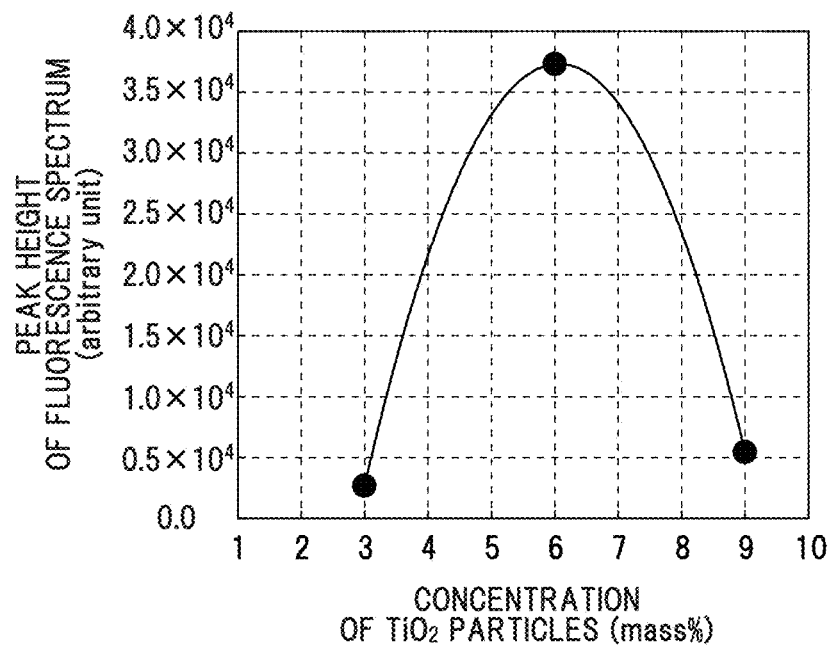
FIGS. 6A and 6B are graphs showing a relationship between the peak height of the fluorescence spectrum in the Raman spectra of the resin composition shown in FIG. 2C and the concentration of $TiO_2$ particles in the resin composition.
Figure 6B:
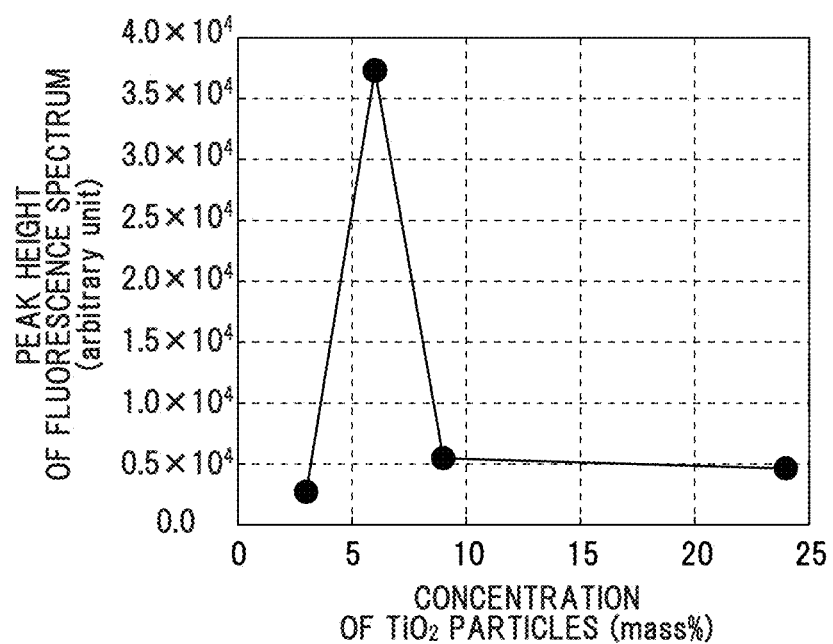

FIG. 5A is a graph showing a relationship between peak height of fluorescence spectrum in the Raman spectra of the resin composition 1a including rutile type TiO$_2$ particles as the TiO$_2$ particles 11a shown in FIG. 2A and the concentration of TiO$_2$ particles 11a in the resin composition 1a. FIG. 5B is a graph showing a relationship between peak height of fluorescence spectrum in the Raman spectra of the resin composition 1a including anatase type TiO$_2$ particles as the TiO$_2$ particles 11$a$ shown in FIG. 2B and the concentration of TiO$_2$ particles 11$a$ in the resin composition 1$a$. FIGS. 6A and 6B are graphs showing a relationship between peak height of fluorescence spectrum in the Raman spectra of the resin composition 1$b$ including anatase type TiO$_2$ particles as the TiO$_2$ particles 11$b$ shown in FIG. 2C and the concentration of TiO$_2$ particles 11$b$ in the resin composition 1$b$.

The peak height of each fluorescence spectrum was obtained by subtracting the intensity of a baseline, which is a straight line connecting a point at 250 cm$^{-1}$ and a point at 4250 cm$^{-1}$ on the fluorescence spectrum, from the highest intensity of the fluorescence spectrum observed in the range of 250 to 4250 cm$^{-1}$. Here, the highest fluorescence spectrum intensity shown in FIG. 2A is the intensity at 575.4 nm (at a Raman shift of 1415.7 cm$^{-1}$) indicated by an arrow, the highest Raman spectrum intensity shown in FIG. 2B is the intensity at 564.2 nm (at a Raman shift of 1070.7 cm$^{-1}$) indicated by an arrow, and the highest Raman spectrum intensity shown in FIG. 2C is the intensity at 548.5 nm (at a Raman shift of 563.3 cm$^{-1}$) indicated by an arrow.

An approximate curve in FIG. 5A is a curve obtained by polynomial approximation using the least-square method and is expressed by the equation $y=-2.0088\times10^3 x^2+2.3683\times10^4 x-4.0506\times10^4$, where x is a value on the horizontal axis and y is a value on the vertical axis. An approximate curve in FIG. 5B is a curve obtained by polynomial approximation using the least-square method and is expressed by the equation $y=-8.20844\times10^2 x^2+9.85013\times10^3 x-1.94984\times10^4$, where x is a value on the horizontal axis and y is a value on the vertical axis. An approximate curve in FIG. 6A is a curve obtained by polynomial approximation using the least-square method and is expressed by the equation $y=-3.69234\times10^3 x^2+4.47697\times10^4 x-9.83856\times10^4$, where x is a value on the horizontal axis and y is a value on the vertical axis.

The graphs in FIGS. 3A, 3B, 4A, 4B, 5A, 5B, 6A, and 6B show that fluorescence intensity is extremely high only when the concentration of the TiO$_2$ particles in the resin composition including silicon rubber as a base material is near 6 mass % regardless of whether the TiO$_2$ particles are rutile type or anatase type. Therefore, when the fluorescence spectrum has a certain degree of intensity, it can be determined that the concentration of the TiO$_2$ particles is near 6 mass %, e.g., at least within a range of 3.4 to 8.1 mass %, even if the exact intensity of the fluorescence spectrum is unknown. In other words, the intensity of the fluorescence spectrum is high enough to be easily determined when the concentration of the TiO$_2$ particles is at least within the range of 3.4 to 8.1 mass %.

Regarding this range of 3.4 to 8.1 mass %, a mean value $\mu$ and a standard deviation $\sigma$ between two points with intensity (integral intensity, peak intensity) of the fluorescence spectrum of 0 were calculated for each of the approximate curves (quadratic curves) in FIGS. 3A, 3B, 4A, 5A, 5B, and 6A and the range of 3.4 to 8.1 mass % was determined as a range including all the obtained ranges of $\mu\pm\sigma$ (rounded down to the nearest tenth to obtain the minimum value, 3.4, and rounded up to the nearest tenth to obtain the maximum value, 8.1). In particular, the range of $\mu\pm\sigma$ obtained from the approximate curve in FIG. 3A was 3.4 to 8.1 mass %, the range of $\mu\pm\sigma$ obtained from the approximate curve in FIG. 3B was 3.9 to 8.0 mass %, the range of $\mu\pm\sigma$ obtained from the approximate curve in FIG. 4A was 4.2 to 7.9 mass %, the range of $\mu\pm\sigma$ obtained from the approximate curve in FIG. 5A was 3.6 to 7.8 mass %, the range of $\mu\pm\sigma$ obtained from the approximate curve in FIG. 5B was 4.0 to 8.1 mass %, the range of $\mu\pm\sigma$ obtained from the approximate curve in FIG. 6A was 4.0 to 8.0 mass %, and 3.4 to 8.1 was obtained as the range including all of these.

Here, the higher the concentration of the TiO$_2$ particles in the resin composition, the more effectively the TiO$_2$ particles shield UV-C light and the higher the resistance of the resin composition to UV-C light, but it has been confirmed that the resistance of the resin composition to UV-C light is sufficient when at least not less than 3.4 mass %. Meanwhile, when the concentration of the TiO$_2$ particles in the resin composition is too high, percent elongation of the resin composition decreases, or the TiO$_2$ particles may not be uniformly dispersed due to aggregation, etc., but it has been confirmed that such problems do not occur when at least not more than 8.1 mass %. That is, when the concentration of the TiO$_2$ particles in the resin composition including silicon rubber as a base material is within the range of 3.4 to 8.1 mass %, the resistance of the resin composition to UV-C light can be increased while suppressing a decrease in percent elongation or quality.

Meanwhile, in each of the Raman spectra in FIGS. 2A to 2C, e.g., a peak assigned to C—H stretching vibration originating from silicone included in the base materials 10$a$, 10$b$ (hereinafter, referred to as C—H stretching vibration peak) can be used as a standard for intensity (integral intensity, peak intensity) of the fluorescence spectrum. That is, it is possible to evaluate the characteristics of the resin composition described above based on values of ratios of integral intensity/peak height of fluorescence spectrum to integral intensity/peak height of the C—H stretching vibration peak in the Raman spectrum. Two peaks exhibiting the highest intensity in a range of 2800 to 3100 cm$^{-1}$ are the C-H stretching vibration peaks. The integral intensity of the C-H stretching vibration peak is a sum of the integral intensities of these two peaks, and the peak height of the C-H stretching vibration peak is the height of the peak of the two which is located on the low wavenumber side (the left side in FIG. 2). The integral intensity and peak height of the C—H stretching vibration peak are calculated by fitting analysis using a statistical distribution function such as Lorentz function, Pseudo-Voigt function, or Gauss distribution function.

Figure 7A:
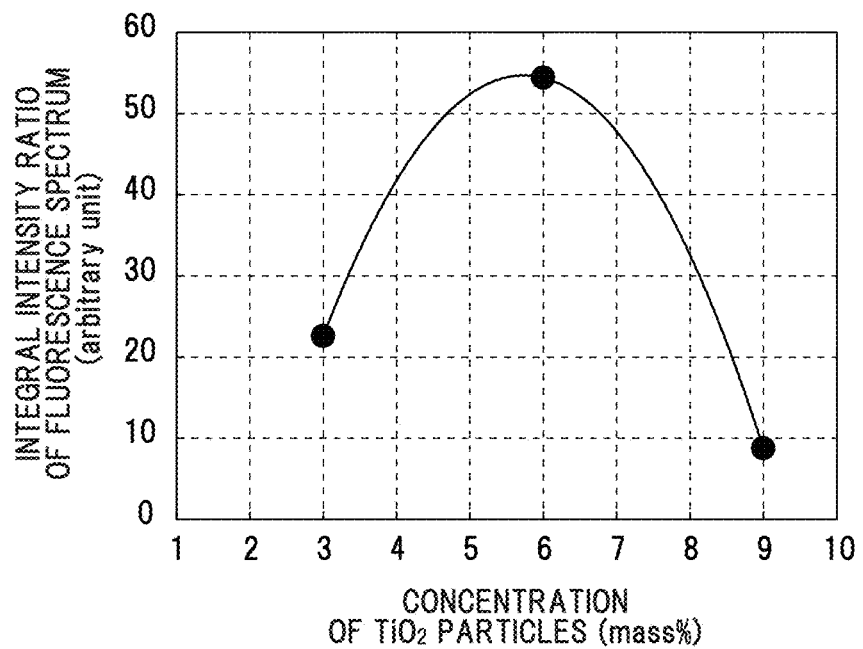
FIG. 7A is a graph showing a relationship between the integral intensity ratio in the Raman spectra of the resin composition shown in FIG. 2A and the concentration of $TiO_2$ particles in the resin composition.
Figure 7B:
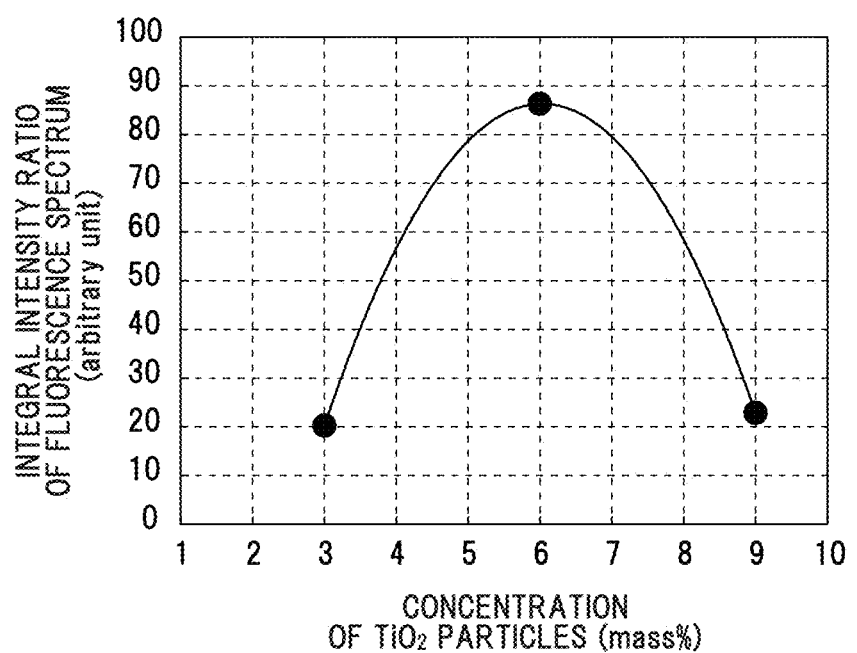
FIG. 7B is a graph showing a relationship between the integral intensity ratio in the Raman spectra of the resin composition shown in FIG. 2B and the concentration of $TiO_2$ particles in the resin composition.
Figure 8A:
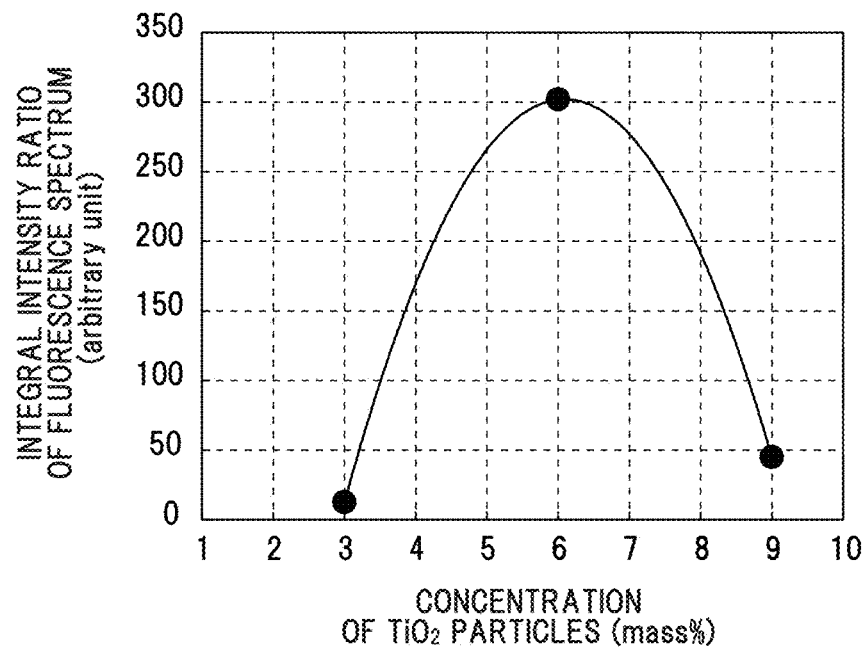
FIGS. 8A and 8B are graphs showing a relationship between the integral intensity ratio in the Raman spectra of the resin composition shown in FIG. 2C and the concentration of $TiO_2$ particles in the resin composition.
Figure 8B:
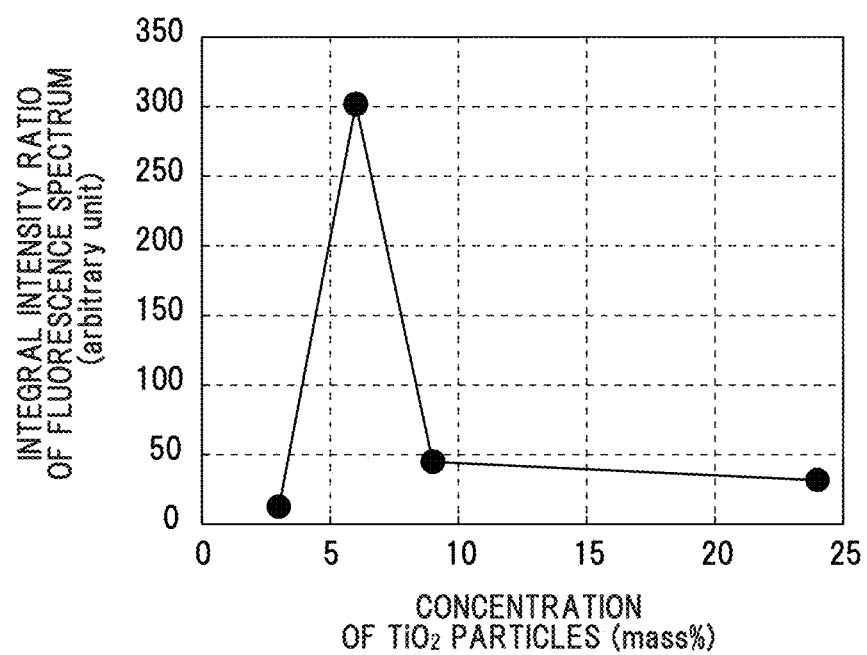

FIG. 7A is a graph showing a relationship between a value of a ratio of the integral intensity of the fluorescence spectrum to the integral intensity of the C—H stretching vibration peak (an integral intensity ratio) in the Raman spectra of the resin composition 1$a$ including rutile type TiO$_2$ particles as the TiO$_2$ particles 11$a$ shown in FIG. 2A and the concentration of the TiO$_2$ particles 11$a$ in the resin composition 1$a$. FIG. 7B is a graph showing a relationship between a value of the ratio of the integral intensity of the fluorescence spectrum to the integral intensity of the C—H stretching vibration peak (the integral intensity ratio) in the Raman spectra of the resin composition 1$a$ including anatase type TiO$_2$ particles as the TiO$_2$ particles 11$a$ shown in FIG. 2B and the concentration of the TiO$_2$ particles 11$a$ in the resin composition 1$a$. FIGS. 8A and 8B are graphs showing a relationship between a value of the ratio of the integral intensity of the fluorescence spectrum to the integral intensity of the C—H stretching vibration peak (the integral intensity ratio) in the Raman spectra of the resin composition 1$b$ including anatase type TiO$_2$ particles as the TiO$_2$ particles 11$b$ shown in FIG. 2C and the concentration of the TiO$_2$ particles 11$b$ in the resin composition 1$b$.

An approximate curve in FIG. 7A is a curve obtained by polynomial approximation using the least-square method and is expressed by the equation $y=-4.30141x^2+4.93110\times$ 10x−8.66383×10, where x is a value on the horizontal axis and y is a value on the vertical axis. An approximate curve in FIG. 7B is a curve obtained by polynomial approximation using the least-square method and is expressed by the equation $y=-7.19385x^2+8.67671\times10x-1.75336\times10^2$, where x is a value on the horizontal axis and y is a value on the vertical axis. An approximate curve in FIG. 8A is a curve obtained by polynomial approximation using the least-square method and is expressed by the equation $y=-3.03490\times10x^2+3.69587\times10^2x-8.23155\times10^2$, where x is a value on the horizontal axis and y is a value on the vertical axis.

Figure 9A:
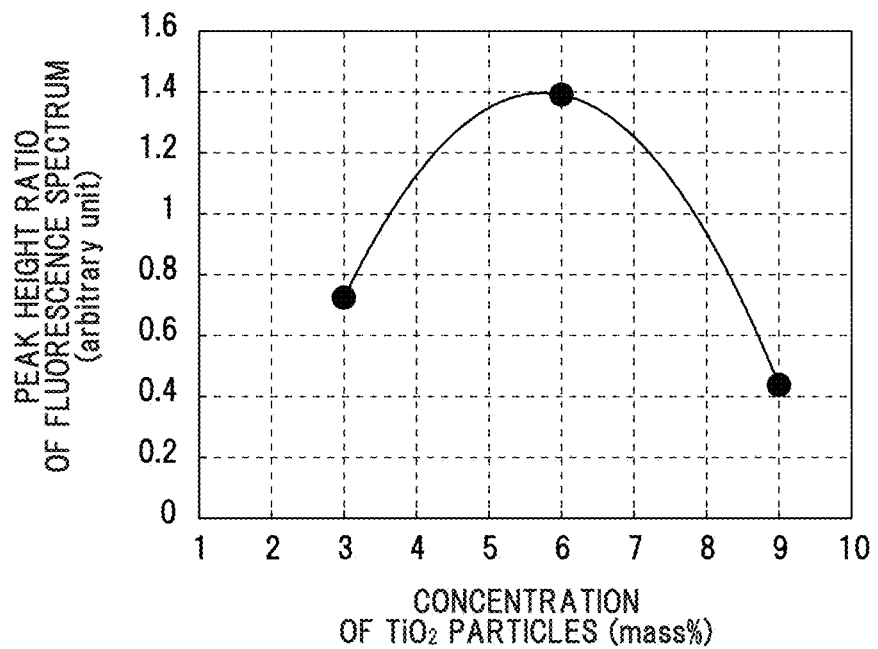
FIG. 9A is a graph showing a relationship between the peak height ratio in the Raman spectra of the resin composition shown in FIG. 2A and the concentration of $TiO_2$ particles in the resin composition.
Figure 9B:
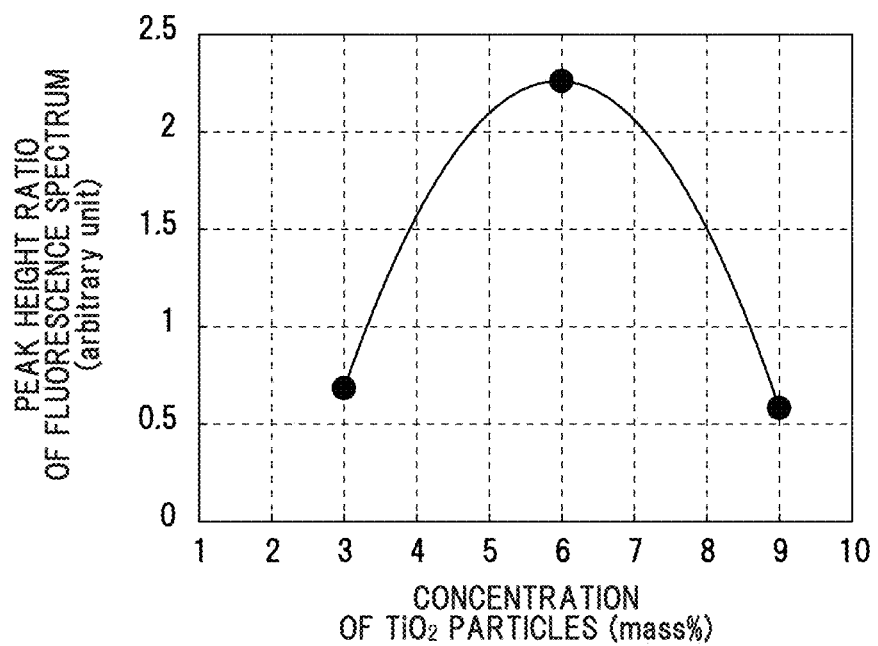
FIG. 9B is a graph showing a relationship between the peak height ratio in the Raman spectra of the resin composition shown in FIG. 2B and the concentration of $TiO_2$ particles in the resin composition.
Figure 10A:
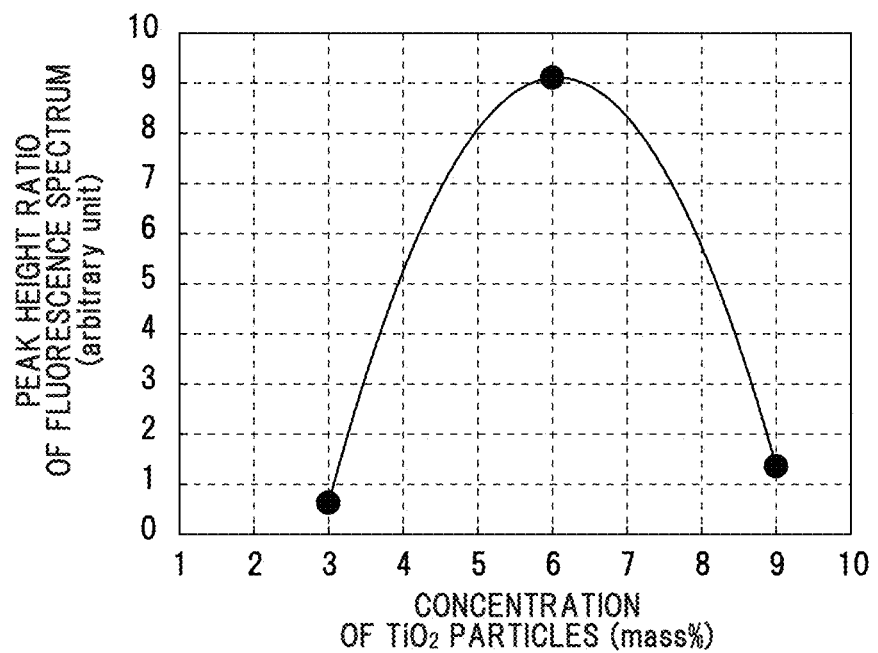
FIGS. 10A and 10B are graphs showing a relationship between the peak height ratio in the Raman spectra of the resin composition shown in FIG. 2C and the concentration of $TiO_2$ particles in the resin composition.

FIG. 9A is a graph showing a relationship between a value of a ratio of peak height of the fluorescence spectrum to peak height of the C—H stretching vibration peak (a peak height ratio) in the Raman spectra of the resin composition 1a including rutile type $TiO_2$ particles as the $TiO_2$ particles 11a shown in FIG. 2A and the concentration of the $TiO_2$ particles 11a in the resin composition 1a. FIG. 9B is a graph showing a relationship between a value of the ratio of the peak height of the fluorescence spectrum to the peak height of the C—H vertical axis. An approximate curve in FIG. 10A is a curve obtained by polynomial approximation using the least-square method and is expressed by the equation $y=-9.01775\times10^{-1}x^2+1.09429x-2.40850\times10$, where x is a value on the horizontal axis and y is a value on the vertical axis.

Table 1 below shows the integral intensity ratio and the peak height ratio for each concentration of the $TiO_2$ particles 11a (rutile type) in the resin composition 1a for each plotted point in FIGS. 7A and 9A, and the respective integral intensities and peak heights of the fluorescence spectrum and the C—H stretching vibration peak for each concentration of the $TiO_2$ particles 11a (rutile type) in the resin composition 1a which were used to calculate the ratios. In this regard, the numerical values of the integral intensity and the peak height of the fluorescence spectrum in Table 1 respectively correspond to the plotted points in FIGS. 3A and 5A.

TABLE 1

Figure 10B:
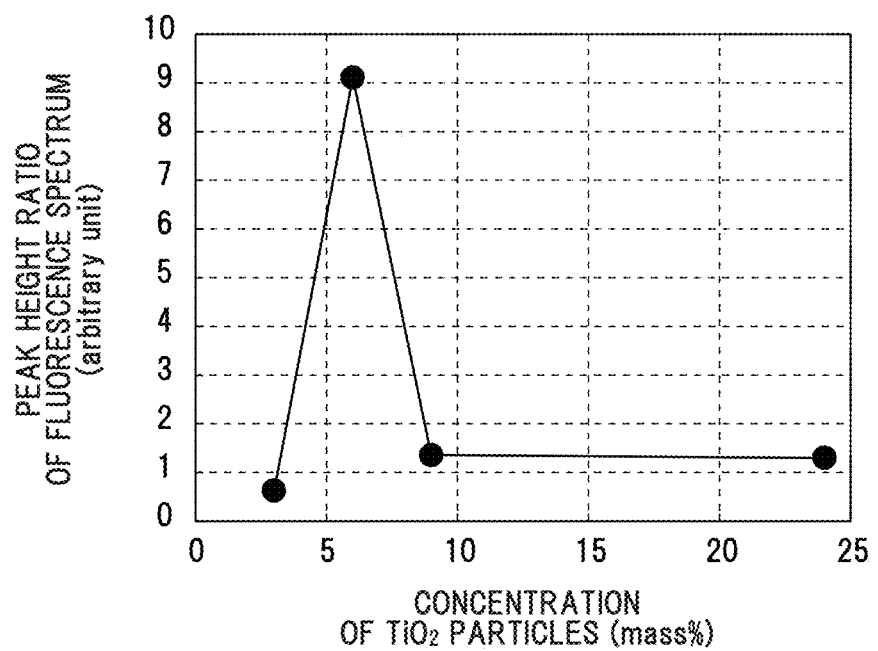

| | | Fluorescence spectrum | | C—H stretching vibration peak | | Integral intensity ratio | Peak height ratio |
|---|---|---|---|---|---|---|---|
| | | Integral intensity | Peak height | Integral intensity | Peak height | | |
| Concentration of $TiO_2$ particles (mass %) | 3 | 19030385 | 12464 | 842716 | 17199 | 22.6 | 0.72 |
| | 6 | 55424178 | 29275 | 1019250 | 21054 | 54.4 | 1.4 |
| | 9 | 9810884 | 9928 | 1121593 | 22671 | 8.75 | 0.44 | stretching vibration peak (the peak height ratio) in the Raman spectra of the resin composition 1a including anatase type $TiO_2$ particles as the $TiO_2$ particles 11a shown in FIG. 2B and the concentration of the $TiO_2$ particles 11a in the resin composition 1a. FIGS. 10A and 10B are graphs showing a relationship between a value of the ratio of peak height of the fluorescence spectrum to the peak height of the C—H stretching vibration peak (the peak height ratio) in the Raman spectra of the resin composition 1b including anatase type $TiO_2$ particles as the $TiO_2$ particles 11b shown in FIG. 2C and the concentration of the $TiO_2$ particles 11b in the resin composition 1b.

Table 2 below shows the integral intensity ratio and the peak height ratio for each concentration of the $TiO_2$ particles 11a (anatase type) in the resin composition 1a for each plotted point in FIGS. 7B and 9B, and the respective integral intensities and peak heights of the fluorescence spectrum and the C—H stretching vibration peak for each concentration of the $TiO_2$ particles 11a (anatase type) in the resin composition 1a which were used to calculate the ratios. In this regard, the numerical values of the integral intensity and the peak height of the fluorescence spectrum in Table 2 respectively correspond to the plotted points in FIGS. 3B and 5B.

TABLE 2

| | | Fluorescence spectrum | | C—H stretching vibration peak | | Integral intensity ratio | Peak height ratio |
|---|---|---|---|---|---|---|---|
| | | Integral intensity | Peak height | Integral intensity | Peak height | | |
| Concentration of $TiO_2$ particles (mass %) | 3 | 3835821 | 2664 | 189699 | 3894 | 20.2 | 0.68 |
| | 6 | 18217533 | 10052 | 211125 | 44484 | 86.3 | 2.3 |
| | 9 | 5144444 | 2664 | 224983 | 4585 | 22.9 | 0.58 |

An approximate curve in FIG. 9A is a curve obtained by polynomial approximation using the least-square method and is expressed by the equation $y=-8.9909\times10^{-2}x^2+1.0311x-1.5594$, where x is a value on the horizontal axis and y is a value on the vertical axis. An approximate curve in FIG. 9B is a curve obtained by polynomial approximation using the least-square method and is expressed by the equation $y=-1.80797\times10^{-1}x^2+2.15236x-4.14563$, where x is a value on the horizontal axis and y is a value on the vertical Table 3 below shows the integral intensity ratio and the peak height ratio for each concentration of the $TiO_2$ particles 11b (anatase type) in the resin composition 1b for each plotted point in FIGS. 8A, 8B, 10A and 10B, and the respective integral intensities and peak heights of the fluorescence spectrum and the C—H stretching vibration peak for each concentration of the $TiO_2$ particles 11b (anatase type) in the resin composition 1b which were used to calculate the ratios. In this regard, the numerical values of the integral intensity and the peak height of the fluorescence spectrum in Table 3 respectively correspond to the plotted points in FIGS. 4A, 4B, 6A and 6B.

TABLE 3

|  |  | Fluorescence spectrum | | C—H stretching vibration peak | | Integral intensity ratio | Peak height ratio |
|---|---|---|---|---|---|---|---|
|  |  | Integral intensity | Peak height | Integral intensity | Peak height | | |
| Concentration of TiO$_2$ particles (mass %) | 3 | 2620199 | 2692 | 210176 | 4289 | 12.5 | 0.63 |
|  | 6 | 55541541 | 37308 | 184030 | 4096 | 302 | 9.1 |
|  | 9 | 8815947 | 5462 | 196499 | 4023 | 44.9 | 1.4 |
|  | 24 | 5533262 | 4615 | 175041 | 3555 | 31.6 | 1.3 |

Values of the ratios of the integral intensity/the peak height of fluorescence spectrum to the integral intensity/the peak height of the C—H stretching vibration peak (the integral intensity ratio and the peak height ratio) do not change even when intensity of the entire spectrum changes, hence, these values do not depend on measurement conditions such as measurement device or measurement temperature. Therefore, by using the integral intensity ratio or the peak height ratio, it is possible to determine the concentration of the TiO$_2$ particles in the resin composition while eliminating the effect of changes in spectral intensity which is dependent on the measurement conditions. Then, for example, it can be determined from FIGS. 7A and 9A that the concentration of rutile type TiO$_2$ particles included in the resin composition 1a is within the range of 3.4 to 8.1 mass % (the range including 3.4 to 8.1 mass %, which is the range of μ±σ obtained from the approximate curve in FIG. 3A, and 3.6 to 7.8 mass %, which is the range of μ±σ obtained from the approximate curve in FIG. 5A) when the integral intensity ratio is not less than 30.5 and the peak height ratio is not less than 0.89, it can be determined from FIGS. 7B and 9B that the concentration of anatase type TiO$_2$ particles included in the resin composition 1a is within the range of 3.9 to 8.1 mass % (the range including 3.9 to 8.0 mass %, which is the range of μ±σ obtained from the approximate curve in FIG. 3B, and 4.0 to 8.1 mass %, which is the range of μ±σ obtained from the approximate curve in FIG. 5B), i.e., within the range of 3.4 to 8.1 mass % when the integral intensity ratio is not less than 36.5 and the peak height ratio is not less than 1.0, and it can be determined from FIGS. 8A and 10A that the concentration of anatase type TiO$_2$ particles included together with the silicone resin particles in the resin composition 1b is within the range of 4.0 to 8.0 mass % (the range including 4.2 to 7.9 mass %, which is the range of μ±σ obtained from the approximate curve in FIG. 4A, and 4.0 to 8.0 mass %, which is the range of μ±σ obtained from the approximate curve in FIG. 6A), i.e., within the range of 3.4 to 8.1 mass % when the integral intensity ratio is not less than 82 and the peak height ratio is not less than 2.6.

In this regard, the reason why the integral intensity ratio in FIG. 8A is extremely higher than the integral intensity ratios in FIGS. 7A, 7B and the peak height ratio in FIG. 10A is extremely higher than the peak height ratios in FIGS. 9A, 9B has not been confirmed, but it is presumed to be due to the silicone resin particles included in the resin composition 1b. One possible hypothesis is that the presence of silicone resin particles increases the region where high fluorescence intensity derived from titanium oxide occurs since the titanium oxide particles aggregate and become dense at the sites between the silicone resin particles. Actually, an aggregated state of titanium oxide between the silicone resin particles has been confirmed by Raman spectroscopy.

In the Raman scattering measurement in the resin composition quality controlling method in the first embodiment, a spot diameter of laser irradiated onto a surface of the resin compositions 1a, 1b is a measuring area, hence, evaluation can be performed within a microscopic region with a diameter of not more than 1 μm (e.g., 0.4 to 1.0 μm). That is, it is possible to obtain not only average information about the concentration of the TiO$_2$ particles 11a, 11b in the resin compositions 1a, 1b but also information for each microscopic region, enabling more precise control of the quality of the resin compositions 1a, 1b. In this regard, the above-mentioned value is not the limit value for the laser spot diameter. In principle, the laser spot diameter is determined by the wavelength of laser source and the numerical aperture of the objective lens. Therefore, when Raman spectroscopy analysis is performed on the resin compositions 1a, 1b by using the laser with a shorter wavelength and an objective lens with a large numerical aperture, it is possible to measure in even smaller microscopic regions of less than 0.4 μm.

In addition, the concentration of the TiO$_2$ particles in the resin compositions 1a, 1b in various forms can be determined by using a gun-type Raman measurement device of which the probe portion including a laser emitting portion and a scattered light receiving portion can be moved freely.

Second Embodiment

The second embodiment of the invention relates to a cable or a tube that includes insulators made of the resin compositions 1a, 1b in the first embodiment. Next, an example of such a cable used for a medical ultrasonic probe cable will be described.

Figure 11:
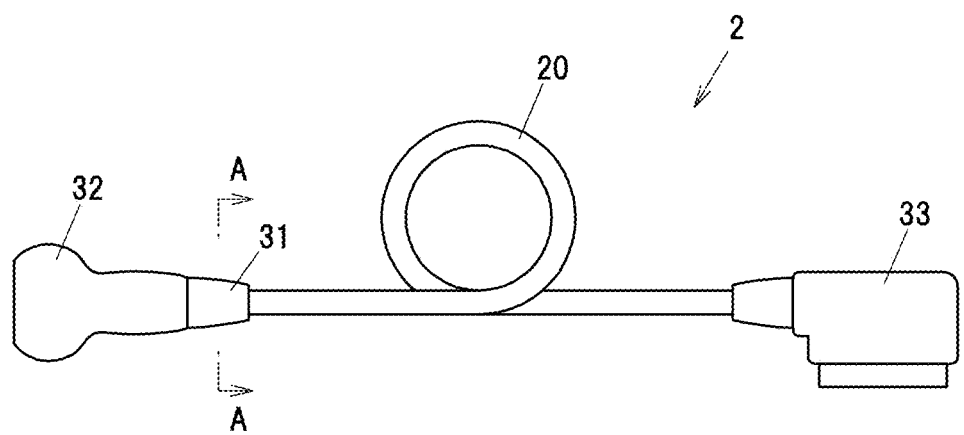
FIG. 11 is a schematic plan view showing a configuration of an ultrasonic probe cable in the second embodiment of the invention.

FIG. 11 is a schematic plan view showing a configuration of an ultrasonic probe cable 2 in the second embodiment of the invention. As shown in FIG. 11, the ultrasonic probe cable 2 is configured such that an ultrasonic probe 32 is attached to an end portion of a cable 20 via a boot 31 protecting the end portion. Then, a connector 33 to be connected to a main body of an ultrasonic imaging device is attached to the other end of the cable 20.

Figure 12A:
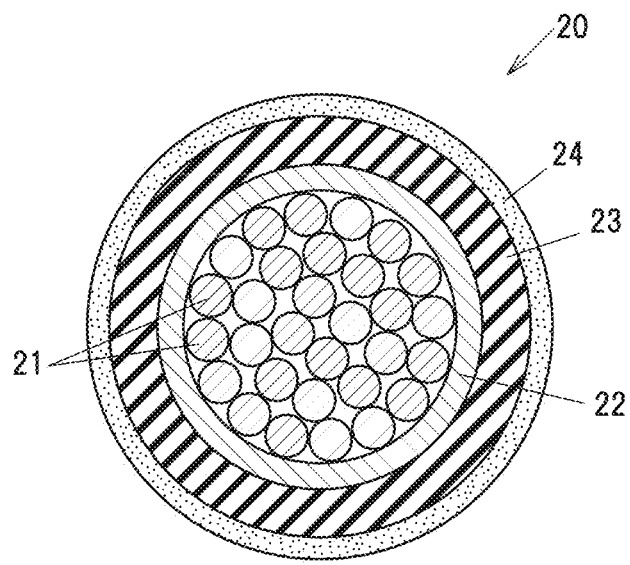
FIG. 12A is a radial cross-sectional view showing a cable of the ultrasonic probe cable.

FIG. 12A is a radial cross-sectional view showing the cable 20 of the ultrasonic probe cable 2. Inside the cable 20, e.g., plural electric wires 21 typified by coaxial cable are housed and a shield 22 such as braided shield is provided so as to cover the plural electric wires 21. Then, a sheath 23 and a coating film 24 thereon are provided so as to cover the shield 22.

Figure 12B:
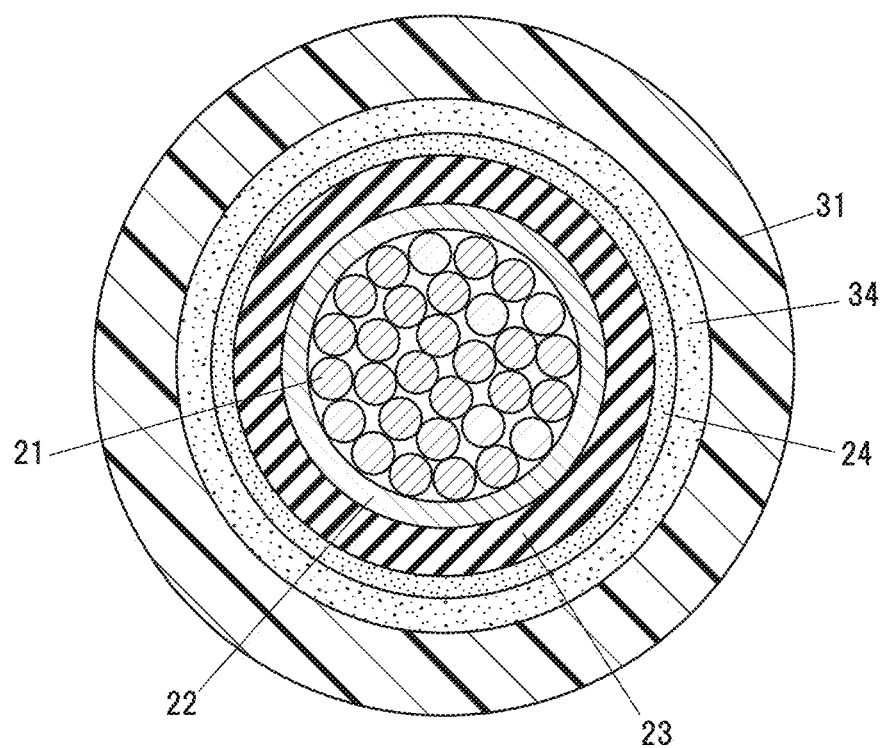
FIG. 12B is a radial cross-sectional view showing the ultrasonic probe cable taken long line A-A shown in FIG. 11.

FIG. 12B is a radial cross-sectional view showing the ultrasonic probe cable 2 taken long line A-A shown in FIG. 11. As shown in FIG. 12B, the boot 31 is attached to the coating film 24 via an adhesive layer 34 so as to cover the coating film 24. The adhesive layer 34 is made of, e.g., a silicone-based adhesive or an epoxy-based adhesive. Meanwhile, the boot 31 may be made of, e.g., PVC, silicone rubber or chloroprene rubber, etc., and preferably includes $TiO_2$ particles to shield UV-C light or an organic UV light absorbing agent in the same manner as the resin composition 1a.

The sheath 23 and the coating film 24 of the cable 20 are respectively made of the resin composition 1a and the resin composition 1b. That is, the cable 20 includes insulators made of the resin compositions 1a, 1b including $TiO_2$ particles dispersed in a base material consisting mainly of a silicone rubber. Here, by using the resin compositions 1a, 1b including the $TiO_2$ particles 11a, 11b with a concentration within the range of 3.4 to 8.1 mass %, it is possible to increase resistance of the cable 20 to UV-C light while suppressing a decrease in percent elongation or quality of the insulators. In addition, since the coating film 24 made of the resin composition 1b includes the irregularity-forming particles 12 and has surface irregularity, the cable 20 is excellent in sliding properties. The $TiO_2$ particles 11a, 11b in the sheath 23 and the coating film 24 are not shown in the drawings.

Even when the cable 20 does not include the coating film 24, it is possible to increase resistance of the cable 20 to UV-C light while suppressing a decrease in percent elongation or quality of the insulators when the resin composition 1a, which includes the $TiO_2$ particles 11a, with a concentration within the range of 3.4 to 8.1 mass %, is used as a material of the sheath 23.

Next, an example of a method for manufacturing the ultrasonic probe cable 2 in the second embodiment will be described. Firstly, plural (e.g., not less than one hundred) electric wires 21 are bundled together. Then, the shield 22 is formed to cover the bundled plural electric wires 21. Subsequently, the sheath 23 made of resin composition 1a and the coating film made of resin composition 1b are formed to cover the shield 22. The sheath 23 is formed by, e.g., extrusion using an extruder. The coating film 24 is formed by, e.g., a dipping method, a spray coating method, a roll coating method.

Next, a configuration of a tube (a hollow tube) used for medical applications such as catheter will be described as another example of the cable and tube including insulators made of the resin compositions 1a, 1b.

Figure 13A:
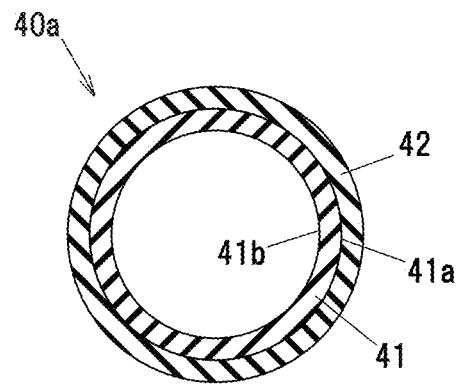
FIGS. 13A to 13C are radial cross-sectional views, respectively showing medical tubes in the second embodiment of the invention.
Figure 13B:
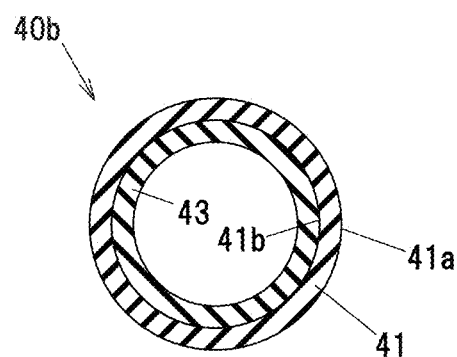
Figure 13C:
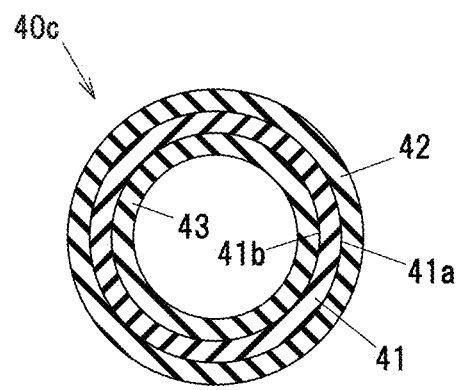

FIGS. 13A to 13C are radial cross-sectional views respectively showing medical tubes in the second embodiment of the invention. A medical tube 40a shown in FIG. 13A includes an outer coating film 42 on an outer surface 41a of a tube main body 41. A medical tube 40b shown in FIG. 13B includes an inner coating film 43 on an inner surface 41b of the tube main body 41. A medical tube 40c shown in FIG. 13C includes the outer coating film 42 and the inner coating film 43 respectively on the outer surface 41a and the inner surface 41b of the tube main body 41.

As exemplified as the medical tubes 40a, 40b, 40c, the tube in the second embodiment includes the tube main body 41, and the outer coating film 42 coating film the outer surface 41a of the tube main body 41, or the inner coating film 43 coating film the inner surface 41b of the tube main body 41, or both the outer coating film 42 and the inner coating film 43.

The medical tubes 40a, 40b, 40c are configured such that the tube main body 41 is made of resin composition 1a, and the outer coating film 42 and the inner coating film 43 are made of the n composition 1b. That is, the medical tubes 40a, 40b, 40c include insulators made of the resin compositions 1a, 1b including the $TiO_2$ particles 11a, 11b dispersed in a base material consisting mainly of silicone rubber. Here, by using the resin compositions 1a, 1b including the $TiO_2$ particles 11a, 11b with a concentration within the range of 3.4 to 8.1 mass %, it is possible to increase the resistance of the medical tube 40a, 40b, 40c to UV-C light while suppressing a decrease in percent elongation or quality. In addition, since the outer coating film 42 and the inner coating film 43 made of the resin composition 1b include the irregularity-forming particles 12 and have surface irregularity, the surfaces of the outer coating film 42 and the inner coating film 43 of the medical tubes 40a, 40b, 40c are excellent in sliding properties. The $TiO_2$ particles 11a, 11b in the tube main body 41, the outer coating film 42, and the inner coating film 43 are not shown in the drawings.

The tube in the second embodiment can be used for, e.g., a tube set for an endoscopic surgical instrument, a tube set for an ultrasonic surgical instrument, a tube for blood analyzer, piping in an oxygen concentrator, a dialysis blood circuit, an artificial cardiopulmonary circuit, and an endotracheal tube, etc.

Even when the medical tubes 40a, 40b, 40c do not include the outer coating film 42 and the inner coating film 43, it is possible to increase the resistance of the medical tubes 40a, 40b, 40c to UV-C light while suppressing a decrease in percent elongation or quality when the resin composition 1a, which includes the $TiO_2$ particles 11a with a concentration within the range of 3.4 to 8.1 mass %, is used as a material of the tube main body 41.

Method for Controlling the Quality of Cable or Tube

According to the second embodiment, as a cable and tube quality controlling method with insulators made of the resin compositions 1a, 1b, it is possible to provide a cable and tube quality controlling method, in which the concentration of the $TiO_2$ particles in an insulator being provided on a cable or a tube and made of the resin composition 1a or the resin composition 1b is determined using the resin composition quality controlling method described above.

Figure 14A:
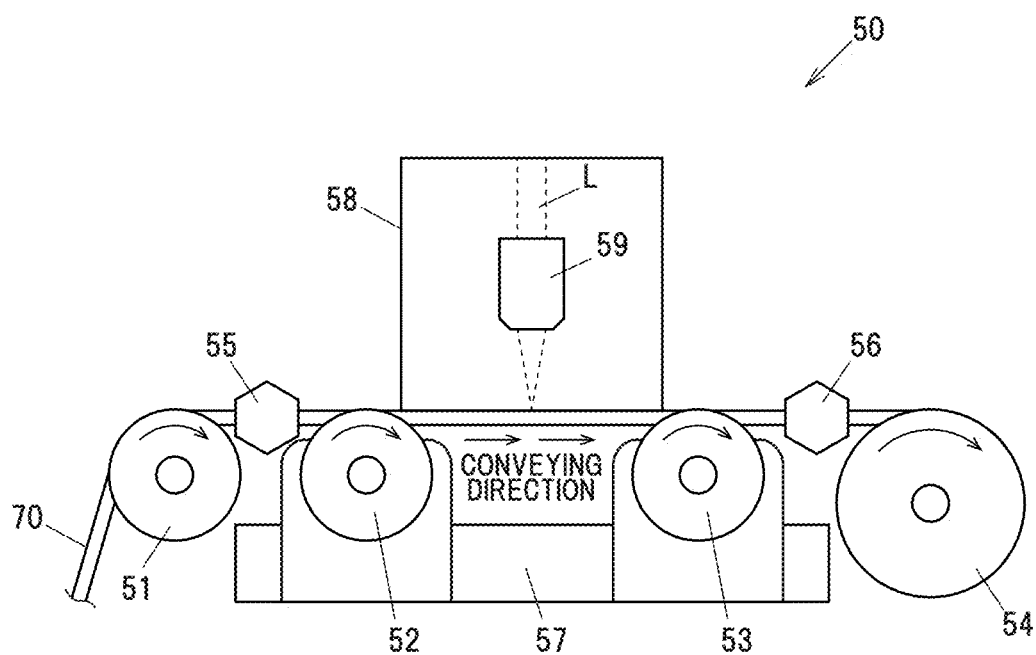
FIGS. 14A and 14B are schematic side and top views showing a configuration example of a cable inspection system used for a method for controlling the quality of a cable.
Figure 14B:
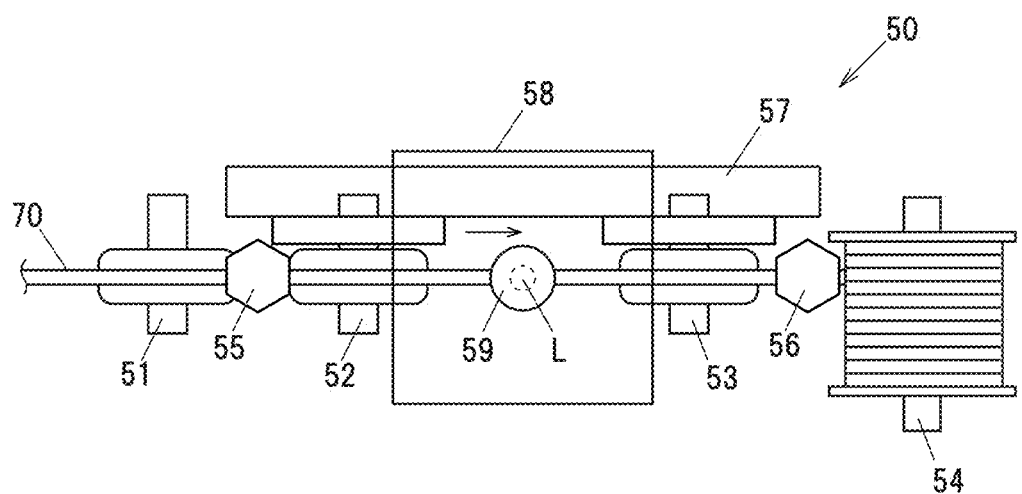

FIGS. 14A and 14B are schematic side and top views showing a configuration example of a cable inspection system 50 used for a method for controlling the quality of a cable. The cable inspection system 50 is capable of inspecting a cable 70 including an insulator (or insulators) made of a resin composition including $TiO_2$ particles dispersed in a base material consisting mainly of silicone rubber, such as the cable 20 described above, and capable of determining the concentration of the $TiO_2$ particles in the insulator.

The cable inspection system 50 includes an introduction reel 51 to introduce the cable 70 into the cable inspection system 50, a sending reel 52 to send out the cable 70 introduced by the introduction reel 51 to the measuring area for Raman scattering measurement, a receiving reel 53 to receive the cable 70 which passed through the measuring area, a wind-up coil 54 to wind up the cable 70 received by the receiving reel 53, a sending guide jig 55 placed between the introduction reel 51 and the sending reel 52 to guide advance of the cable 70, a receiving guide jig 56 placed between the receiving reel 53 and the wind-up coil 54 to guide advance of the cable 70, a support 57 to support the sending reel 52 and the receiving reel 53, etc., and a Raman measurement device 58 to perform measurement on the insulator of the cable 70 in the measuring area between the sending reel 52 and the receiving reel 53.

Regarding the Raman measurement device 58, only a probe portion thereof is schematically shown in FIGS. 14A and 14B. The probe portion of the Raman measurement device 58 has an objective lens 59 that focuses laser light L to the insulator of the cable 70.

With the cable inspection system 50, it is possible to determine the concentration of $TiO_2$ particles in the insulator(s) in the original state of the cable 70 without destroying the cable 70.

Figure 15:
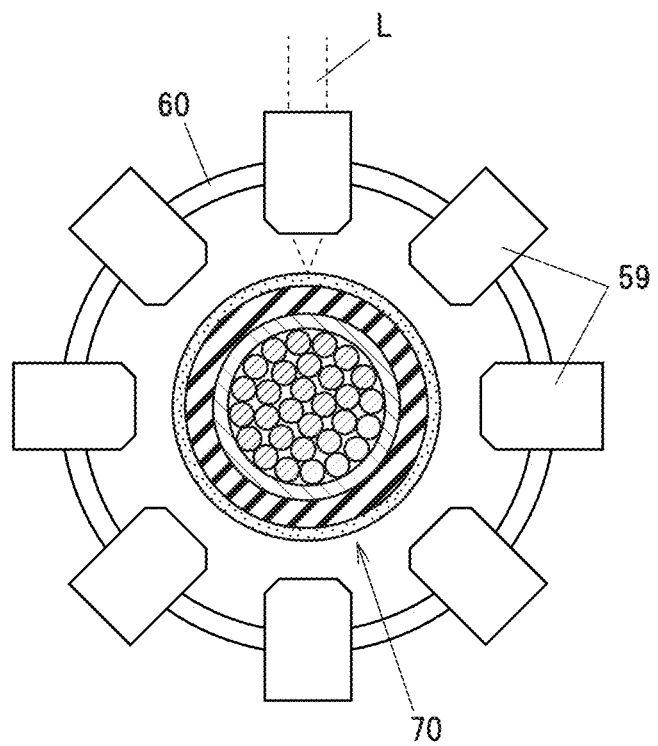
FIG. 15 is a schematic diagram illustrating a probe portion of a Raman measurement device that includes a circumference measuring unit.

The probe portion of the Raman measurement device 58 may include a circumference measuring unit 60 which has plural objective lenses 59 arranged to surround the cable 70, as shown in FIG. 15. Raman scattering measurement can be performed over the entire circumference of the cable 70 by using the circumference measuring unit 60. Alternatively, the circumference measuring unit 60 may have a structure to perform Raman scattering measurement over the entire circumference of the cable 70 by moving one objective lens 59 along the circumferential direction of the cable 70. In addition, the Raman measurement device 58 may be a gun-type Raman measurement device of which the probe portion can be moved freely.

The Raman measurement device 58 may be connected to a determination device that determines the concentration of the $TiO_2$ particles in the insulator(s) of the cable 70 based on the intensity of the fluorescence spectrum in the Raman spectrum. This determination device is, e.g., a personal computer with a program to perform the above-mentioned determination stored in storage. This determination device can be also used for quality control of resin compositions such as the resin compositions 1a, 1b in a form other than the insulator of the cable 70. That is, according to the invention, it is possible to provide a determination device capable of performing the above-described determination step in the method for controlling the quality of the resin composition.

The Raman measurement device 58 also can perform the measurement step by Raman scattering measurement in the method for controlling the quality of the cable in the second embodiment. The Raman measurement device 58 can be also used for the measurement of resin compositions such as the resin compositions 1a, 1b in a form other than the insulators of the cable 70. That is, according to the invention, it is possible to provide an inspection system that includes the Raman measurement device 58 capable of performing the above-described measurement step in the method for controlling the quality of the resin composition, and the determination device capable of performing the above-described determination step in the method for controlling the quality of the resin composition.

Effects of the Embodiments

According to the first embodiment, the concentration of the $TiO_2$ particles in the resin composition can be determined using Raman scattering measurement, to provide a resin composition having excellent resistance to UV-C light and in which a decrease in percent elongation and quality is suppressed.

According to the second embodiment, it is possible to provide a cable or a tube that includes insulators made of resin compositions including $TiO_2$ particles dispersed in a base material consisting mainly of silicone rubber and configured to have a $TiO_2$ particle concentration within the range of 3.4 to 8.1 mass % and has excellent resistance to UV-C light and in which a decrease in percent elongation and quality of the insulators is suppressed. In addition, according to the second embodiment, the concentration of the $TiO_2$ particles in the insulators of the cable or the tube can be determined using Raman scattering measurement, to provide a cable or a tube which has excellent resistance to UV-C light and in which a decrease in percent elongation and quality of the insulators is suppressed.

In addition, the resin composition quality controlling method, the cable and tube quality controlling method, and the determination device and the inspection system used in the cable and tube quality controlling method, etc., according to the embodiments described above can be also applied to material development using Materials Informatics (MI) which uses machine learning or artificial intelligence (AI), etc., to analyze data.

SUMMARY OF THE EMBODIMENTS

Technical ideas understood from the embodiments will be described below citing the reference signs, etc., used for the embodiments. However, each reference sign, etc., described below is not intended to limit the constituent elements in the claims to the members, etc., specifically described in the embodiments.

According to the feature [1], a resin composition quality controlling method includes: measuring a Raman spectrum of a resin composition 1a, 1b comprising $TiO_2$ particles 11a, 11b dispersed in a base material 10a, 10b comprising mainly a silicone rubber by irradiating the resin composition 1a, 1b with laser; and determining a concentration of the $TiO_2$ particles 11a, 11b in the resin composition 1a, 1b based on the intensity of a fluorescence spectrum in the Raman spectrum.

According to the feature [2], in the resin composition quality controlling method defined by the feature [1], in the determining, determination of whether or not the concentration of the $TiO_2$ particles 11a, 11b in the resin composition 1a, 1b is within a range of 3.4 to 8.1 mass % is made.

According to the feature [3], in the resin composition quality controlling method defined by the feature [2], in the determining, the determination is made based on a value of a ratio of the intensity of the fluorescence spectrum to an intensity of a peak assigned to C—H stretching vibration in the Raman spectrum.

According to the feature [4], in the resin composition quality controlling method defined by the feature [3], in the determining, the determination is made based on whether or not a value of a ratio of an integral intensity of the fluorescence spectrum to an integral intensity of the peak assigned to C—H stretching vibration in the Raman spectrum is not less than 30.5 when the $TiO_2$ particles are rutile type.

According to the feature [5], in the resin composition quality controlling method defined by the feature [3], in the determining, the determination is made based on whether or not a value of a ratio of a peak height of the fluorescence spectrum to a peak height of the peak assigned to C—H stretching vibration in the Raman spectrum is not less than 0.89 when the $TiO_2$ particles are rutile type.

According to the feature [6], in the resin composition quality controlling method defined by the feature [3], in the determining, the determination is made based on whether or not the value of the ratio of the integral intensity of the fluorescence spectrum to the integral intensity of the peak assigned to C—H stretching vibration in the Raman spectrum is not less than 36.5 when the $TiO_2$ particles are anatase type.

According to the feature [7], in the resin composition quality controlling method defined by the feature [3], in the determining, the determination is made based on whether or not the value of the ratio of the peak height of the fluorescence spectrum to the peak height of the peak assigned to C—H stretching vibration in the Raman spectrum is not less than 1.0 when the $TiO_2$ particles are anatase type.

According to the feature [8], in the resin composition quality controlling method defined by the feature [3], in the determining, the determination is made based on whether or not the value of the ratio of the integral intensity of the fluorescence spectrum to the integral intensity of the peak assigned to C—H stretching vibration in the Raman spectrum is not less than 82 when the resin composition comprises silicone resin particles and the $TiO_2$ particles are anatase type.

According to the feature [9], in the resin composition quality controlling method defined by the feature [3], in the determining, the determination is made based on whether or not the value of the ratio of the peak height of the fluorescence spectrum to the peak height of the peak assigned to C—H stretching vibration in the Raman spectrum is not less than 2.6 when the resin composition comprises silicone resin particles and the $TiO_2$ particles are anatase type.

According to the feature [10], a cable and tube quality controlling method, includes: determining a concentration of the $TiO_2$ particles 11a, 11b in an insulator 23, 24, 41, 42, 43 being provided on a cable 20 or a tube 40a, 40b, 40c and comprising the resin composition 1a, 1b by the resin composition quality controlling method defined by any one of the features [1] to [9].

According to the feature [11], a determination device configured to perform the determining in the resin composition quality controlling method 1a, 1b defined by any one of the features [1] to [9].

According to the feature [12], an inspection system 50 includes: a Raman measurement device 58 configured to perform the measuring in the resin composition quality controlling method defined by any one of the features [1] to [9]; and a determination device configured to perform the determining in the resin composition quality controlling method 1a, 1b defined by any one of the features [1] to [9].

According to the feature [13], a cable 20 or a tube 40a, 40b, 40c, includes: an insulator 23, 24, 41, 42, 43 comprising a resin composition 1a, 1b comprising $TiO_2$ particles 11a, 11b dispersed in a base material 10a, 10b comprising mainly a silicone rubber, wherein a concentration of the $TiO_2$ particles 11a, 11b in the insulator 23, 24, 41, 42, 43 is within a range of 3.4 to 8.1 mass %.

Although the embodiments of the invention have been described, the invention according to claims is not to be limited to the embodiments described above, and the various kinds of modifications can be implemented without departing from the gist of the invention. In addition, the invention according to claims is not to be limited to the above-mentioned embodiments. Further, please note that not all combinations of the features described in the embodiments are necessary to solve the problem of the invention.

The invention claimed is:

1. A resin composition quality controlling method, comprising:
   measuring a Raman spectrum of a resin composition comprising $TiO_2$ particles dispersed in a base material comprising mainly a silicone rubber by irradiating the resin composition with laser; and
   determining a concentration of the $TiO_2$ particles in the resin composition based on an intensity of a fluorescence spectrum in the Raman spectrum.

2. The method according to claim 1, wherein in the determining, determination of whether or not the concentration of the $TiO_2$ particles in the resin composition is within a range of 3.4 to 8.1 mass % is made.

3. The method according to claim 2, wherein in the determining, the determination is made based on a value of a ratio of the intensity of the fluorescence spectrum to an intensity of a peak assigned to C—H stretching vibration in the Raman spectrum.

4. The method according to claim 3, wherein in the determining, the determination is made based on whether or not a value of a ratio of an integral intensity of the fluorescence spectrum to an integral intensity of the peak assigned to C—H stretching vibration in the Raman spectrum is not less than 30.5 when the $TiO_2$ particles are rutile type.

5. The method according to claim 3, wherein in the determining, the determination is made based on whether or not a value of a ratio of a peak height of the fluorescence spectrum to a peak height of the peak assigned to C—H stretching vibration in the Raman spectrum is not less than 0.89 when the $TiO_2$ particles are rutile type.

6. The method according to claim 3, wherein in the determining, the determination is made based on whether or not the value of the ratio of the integral intensity of the fluorescence spectrum to the integral intensity of the peak assigned to C—H stretching vibration in the Raman spectrum is not less than 36.5 when the $TiO_2$ particles are anatase type.

7. The method according to claim 3, wherein in the determining, the determination is made based on whether or not the value of the ratio of the peak height of the fluorescence spectrum to the peak height of the peak assigned to C—H stretching vibration in the Raman spectrum is not less than 1.0 when the $TiO_2$ particles are anatase type.

8. The method according to claim 3, wherein in the determining, the determination is made based on whether or not the value of the ratio of the integral intensity of the fluorescence spectrum to the integral intensity of the peak assigned to C—H stretching vibration in the Raman spectrum is not less than 82 when the resin composition comprises silicone resin particles and the $TiO_2$ particles are anatase type.

9. The method according to claim 3, wherein in the determining, the determination is made based on whether or not the value of the ratio of the peak height of the fluorescence spectrum to the peak height of the peak assigned to C—H stretching vibration in the Raman spectrum is not less than 2.6 when the resin composition comprises silicone resin particles and the $TiO_2$ particles are anatase type.

10. A cable and tube quality controlling method, comprising:
    determining a concentration of the $TiO_2$ particles in an insulator being provided on a cable or a tube and comprising the resin composition by the resin composition quality controlling method according to claim 1.

11. A determination device configured to perform the determining in the resin composition quality controlling method according to claim 1.

12. An inspection system, comprising:
    a Raman measurement device configured to perform the measuring in the resin composition quality controlling method according to claim 1.

13. An inspection system, comprising:
    a determination device configured to perform the determining in the resin composition quality controlling method according to claim 1.

* * * * *